United States Patent [19]

Forkey

[11] Patent Number: 5,733,246
[45] Date of Patent: Mar. 31, 1998

[54] VIEWING SCOPE WITH IMAGE INTENSIFICATION

[75] Inventor: Richard E. Forkey, Westminster, Mass.

[73] Assignee: Precision Optics Corporation, Gardner, Mass.

[21] Appl. No.: 626,572

[22] Filed: Apr. 2, 1996

Related U.S. Application Data

[63] Continuation of Ser. No. 511,047, Aug. 3, 1995, abandoned, which is a continuation of Ser. No. 242,359, May 13, 1994, abandoned.

[51] Int. Cl.$^6$ ...................................................... A61B 1/04
[52] U.S. Cl. ........................... 600/160; 600/109; 600/921; 348/70; 348/71
[58] Field of Search .................................. 600/109, 112, 600/160, 921; 348/70, 71, 76, 223, 268–270, 647, 665

[56] References Cited

U.S. PATENT DOCUMENTS

| | | |
|---|---|---|
| 3,231,746 | 1/1966 | Goodrich . |
| 3,267,283 | 8/1966 | Kapany . |
| 3,691,302 | 9/1972 | Gaebele et al. . |
| 4,374,325 | 2/1983 | Howorth . |
| 4,602,281 | 7/1986 | Nagasaki et al. . |
| 4,611,920 | 9/1986 | Tsuchiya . |
| 4,646,166 | 2/1987 | Arlan . |
| 4,713,683 | 12/1987 | Fujimori et al. . |
| 4,736,734 | 4/1988 | Mastsuura et al. . |
| 4,742,388 | 5/1988 | Cooper et al. . |
| 4,800,424 | 1/1989 | Noguchi . |
| 4,816,909 | 3/1989 | Kimura et al. . |
| 4,821,116 | 4/1989 | Nagasaki et al. . |
| 4,821,117 | 4/1989 | Sekiguchi . |
| 4,831,437 | 5/1989 | Nishioka et al. ............... 348/71 |
| 4,862,873 | 9/1989 | Vajima et al. . |
| 4,866,526 | 9/1989 | Ams et al. . |
| 4,878,113 | 10/1989 | Nakamura . |
| 4,882,619 | 11/1989 | Hasegawa et al. . |
| 4,926,247 | 5/1990 | Nagasaki et al. . |
| 4,947,246 | 8/1990 | Kikuchi . |
| 4,951,133 | 8/1990 | Onoda . |
| 4,951,134 | 8/1990 | Nakasima et al. ............... 348/71 |
| 4,974,066 | 11/1990 | Tushji . |
| 4,974,090 | 11/1990 | Kawamura et al. . |
| 4,974,936 | 12/1990 | Ams et al. . |
| 4,980,772 | 12/1990 | Kawamura et al. . |
| 4,987,884 | 1/1991 | Nishioka et al. . |
| 4,993,404 | 2/1991 | Lane . |
| 4,998,166 | 3/1991 | Salvati . |
| 5,029,963 | 7/1991 | Naselli et al. . |
| 5,032,913 | 7/1991 | Hattori et al. . |
| 5,078,150 | 1/1992 | Hara et al. . |
| 5,136,153 | 8/1992 | Komiya et al. . |
| 5,153,717 | 10/1992 | Nitta . |
| 5,162,647 | 11/1992 | Field, Jr. . |
| 5,241,170 | 8/1993 | Field, Jr. et al. ............... 606/15 |
| 5,394,187 | 2/1995 | Shipp ............... 348/269 |

*Primary Examiner*—Richard J. Apley
*Assistant Examiner*—John Leubecker
*Attorney, Agent, or Firm*—Pearson & Pearson

[57] ABSTRACT

A viewing scope and related apparatus for producing high quality color images with low levels of object illumination. A light source illuminates the object with a timed, patterned sequence of light at different wavelengths. Light reflected from an object transfers through the viewing scope to an image intensifier and video camera for producing a video signal. A video processor synchronized to the light source converts the video signal into discrete image frames corresponding to the light reflected at each discrete wavelength. An image memory retains each frame for conversion into a color video signal that produces a color display of the object being viewed.

21 Claims, 4 Drawing Sheets

VIEWING SCOPE WITH IMAGE INTENSIFICATION

This application is a continuation of application Ser. No. 08/511,047, filed on Aug. 3, 1995, now abandoned, which is a continuation of application Ser. No. 08/242,359, filed May 13, 1994, now abandoned.

BACKGROUND OF THE INVENTION

1. Field of the Invention

This invention generally relates to viewing scopes and viewing scope apparatus for obtaining images from remote locations in medical and industrial applications. More particularly, this invention relates to an improved viewing scope apparatus that can obtain color images of dimly illuminated objects.

2. Description of Related Art

Viewing scopes that enable one to view the interior of a remote chamber are well known in the art. In an industrial environment, a remote chamber might comprise the interior of a machine, such as a jet engine. Viewing scopes used in such applications are called "borescopes". In medical applications the remote chamber can comprise a passageway in the body. Generally, viewing scopes for such medical applications are called "endoscopes". Often times endoscopes have alternative names that derive from their intended uses. "Laparoscopes" and "bronchoscopes" are examples. In the following discussion the phrase "viewing scope" includes both (1) borescopes and (2) endoscopes in any form including laparoscopes, bronchoscopes and other medical viewing scopes.

Each such viewing scope is an elongated, slender, tubular, optical instrument used as a viewing system for a particular application, and this application determines both the length and diameter of the viewing scope. Each viewing scope generally has an objective at a distal end of the viewing scope and an eyepiece at the proximal end. The objective forms a real image at an objective image plane of objects in a field of view. The eyepiece enables an image at an eyepiece image plane to be viewed. The eyepiece normally conveys this image directly to a human eye or to a television or photographic camera.

Normally the objective and eyepiece are spaced to provide the required working length, so there is a predetermined distance between the objective and eyepiece image planes. Consequently, the housing also carries an image transfer device for presenting an image at the eyepiece image plane with substantially the same brightness, spatial resolution and contrast resolution or modulation as the image at the objective image plane.

Image transfer devices generally take one of three forms based upon the use of (1) optical fibers, (2) rod lenses, or (3) a combination of relay and field lenses. The design process for an image transfer device of any of these forms includes a consideration of a number of factors. Brightness, spatial resolution and contrast modulation are primary design factors. Other factors include aberrations, such as field curvature, astigmatism and color. However, if an image transfer device is well designed, the objective and/or eyepiece can compensate any aberrations that the image transfer device may introduce.

In many applications the design objectives of the viewing scope and the optical system that viewing scope contains are antithetical. Normally optical systems achieve the objectives of maximum brightness, spatial and contrast modulation and true color rendition by proper choice of the effective aperture of the optical system or by controlling the level of the illuminating light or both. However, the design objectives for viewing scopes, particularly for medical applications, usually require that the overall diameter of the viewing scope be kept at a minimum dimension and that the cross section occupied by the optical system be minimized in order to accommodate working channels that enable the operation of apparatus at the distal end of the viewing scope. This constraint constitutes a practical limit on effective aperture size.

As known, the effective light from the optical system varies as the square of the aperture, so limiting or reducing the effective aperture of the system can require a significant increase in the level of the illuminating light on the remote object. This leads to an increase in localized heating due to increased brightness of the light source. In many applications, particularly medical applications, such increase localized heating will not be acceptable. Consequently, the design of a particular viewing scope requires a compromise between these competing or conflicting design objectives. In some situations, that compromise might even include accepting the display of a monochrome image.

It would also be desirable if viewing scopes provided the capability of viewing images in three dimensions. Such a capability, however, requires discrete optical channels and further increases difficulties in reaching a reasonable compromise over the conflicting criteria of viewing scope size, effective aperture and light source brightness. In many situations no compromise is possible, so the viewing scope provides only a planar image.

In attempts to overcome the limits imposed on viewing scope design, some prior art viewing scope systems utilize color switching apparatus to obtain a good color video image of an object at the distal end of the viewing scope. The following patents disclose such prior art systems:

4,713,683 (1987) Fujimori et al.
4,736,734 (1988) Matsuura et al.
4,742,388 (1988) Cooper et al.
4,800,424 (1989) Noguchi
4,816,909 (1989) Kimura et al.
4,821,116 (1989) Nagasaki et al.
4,866,526 (1989) Ams et al.
4,878,113 (1989) Nakamura
4,951,133 (1990) Onoda
4,974,936 (1990) Ams et al.
4,987,884 (1991) Nishioka et al.
5,078,150 (1992) Hara et al.

U.S. Pat. No. 4,713,683 discloses apparatus for displaying a color image obtained from an endoscope on a video monitor. A rotating color disc interposed between an object and a light source produces a sequence of monochrome colors at different wavelengths for illuminating the object. The rotating color disc operates in synchronism with image memories that record, in each, successive frames obtained while a corresponding monochrome color illuminates the object.

Further developments of such systems have also been undertaken. For example, U.S. Pat. No. 4,736,734 discloses an analogous system that has the added capability of varying the angle of view of the optical system and an image enlargement processor with two frame memories that enlarge the image in horizontal and vertical directions respectively. In U.S. Pat. No. 4,742,388 a light source directs sequential fields of red, green and blue light into a cavity. A video processor converts the signal from an image sensor into a composite video signal and a plurality of color filters alter the true color the image appearing on the monitor.

In U.S. Pat. No. 4,800,424, a light source includes a lamp that flashes to control the emitted light amounts of the colored light from a rotary filter fitted with diverse color filters. U.S. Pat. No. 4,816,909 discloses an endoscope with a color imaging device and a signal processor that controls the gain of color signals. In addition, the signal processor uses the number of pixels in the detected image to obtain a final image. The endoscope in U.S. Pat. No. 4,821,116 includes a solid-state pickup element and a light control in the form of a liquid crystal filter that extinguishes the light during each interval that a signal is being read from the solid-state pick up element.

Further modifications are shown in U.S. Pat. No. 4,866,526 in which a lamp is pulsed to control the light flux emitted by the lamp as a function of the actual value of the amplitude of the video signal. In U.S. Pat. No. 4,878,113 a video apparatus associated with an endoscope separates an object image into images at a plurality of wavelengths. U.S. Pat. No. 4,951,133 discloses an endoscope with a rotary filter apparatus that transmits sequentially the illuminating light of diverse wavelengths and that includes apparatus for changing the character of the light, as by obstructing the transmission of infrared rays. In U.S. Pat. No. 4,974,936 a rotary filter apparatus includes a color wheel and a runner wheel that provide discrete pulses of light at different wavelengths. U.S. Pat. No. 4,987,884 also discloses an endoscope using a solid-state image pickup device. In this patent a filter is arranged in the foreground of the pickup device. This filter removes components of light having such wavelengths as are not useful for an observation. The filter may be a component of the objective lens. An endoscope in U.S. Pat. No. 5,078,150 includes a sequential illuminating light source and storage means that store spectral data for enabling a spectral distribution calculation to be performed on the image obtained from the endoscope.

In general optical applications, image intensifiers are often used to enhance the brightness of an image that is dimly illuminated. Such image intensifiers, however, produce essentially monochromatic outputs. The following patents disclose the use of such image intensifiers in viewing scopes and other devices:

| | |
|---|---|
| 3,231,746 | (1966) Goodrich |
| 3,267,283 | (1966) Kapany |
| 4,374,325 | (1983) Howorth |
| 4,821,117 | (1989) Sekiguchi |
| 4,993,404 | (1991) Lane |

U.S. Pat. No. 3,231,746 discloses an image intensifier device using an electron multiplier for providing color intensification. Rotatable color wheels are positioned on opposite sides of the image intensifier to alter the wavelength of the reflected image that reaches various portions of the image intensifier in sequence.

In U.S. Pat. No. 3,267,283 X-rays from an object energize scintillator crystals that are responsive to different energy levels. The light from these crystals enters an image intensifier. The intensified signals then are applied to clusters of fibers of different colors corresponding to the position of crystals of different energy levels. Consequently, the apparatus in this patent displays a color pattern corresponding to the distribution of X-ray energy.

U.S. Pat. No. 4,374,325 discloses an image intensifier with color filters on its input and output surfaces so as to intensify a color image without losing color content. The various filter elements are aligned precisely in both the input and output filters.

In accordance with U.S. Pat. No. 4,821,117 an endoscope views an internal organ having a fluorescent coating. A light source illuminates the area intermittently to obtain a corresponding video image. Alternately a laser irradiates the object to excite the fluorescent material and produce an image. An image intensifier receives this second image, but not the first. The first image and the intensified second image are displayed simultaneously.

U.S. Pat. No. 4,993,404 discloses a fluoroscopy switching device for viewing the outputs from a fluoroscope and an endoscope. In this apparatus an image intensifier is located to receive X-rays emerging from a patient prior to being received in a video camera. The image intensifier is not used in connection with the image from the endoscope.

Each of these patents discloses various approaches for enhancing the color display of images. Some change the wave length of the light striking an object. Others change the wavelength of the light reflected from the object. Still others disclose the use of image intensifiers in connection with monochromatic viewing systems. Notwithstanding this prior art, viewing scopes, particularly medical endoscopes, still require rather bright light sources that are usually specially made for these applications in order to achieve reasonable image characteristics. Moreover, these bright light sources are even required when color enhancement is attempted with apparatus using rotating color filters and image processing systems. Further, the various constraints imposed on such viewing scopes precludes the possibility of using any of these structures for adapting a viewing scope for producing stereo images.

SUMMARY

Therefore, it is an object of this invention to provide a viewing scope for dimly illuminated objects that provides color images with good characteristics.

Another object of this invention is provide a viewing scope that produces, for a dimly lit object, images of good brightness, spatial and contrast resolution and color rendition.

Yet another object of this invention is to provide an optical system for providing color displays of images obtained by endoscopes.

Still another object of this invention is to provide an optical system for providing stereo color displays of images obtained by endoscopes.

Still yet another object of this invention is to provide an optical system for providing color displays of images obtained by endoscopes that minimizes the volume of the endoscope dedicated to the optical system.

Yet still another object of this invention is to provide an endoscope that can produce high-quality color images of an object using low levels of illumination.

In accordance with one aspect of this invention, a viewing scope includes a light transmitter for directing onto the object an iterative, timed, patterned sequence of light at different wavelengths and imaging apparatus for forming at the proximal end an image of the object in response to the light from said light transmission means. A monochrome image intensifier converts the image from said imaging apparatus into a monochrome image for each wavelength of light in the pattern that illuminates the object. An image processor integrates a succession of image frames produced during each pattern iteration to produce on a viewing screen an integrated color image of the object.

In accordance with another aspect of this invention, an endoscopic viewing apparatus for viewing from a proximal end thereof objects at a distal end located in an individual's body includes a tubular housing extending between the proximal and distal ends. The tubular housing carries a light transmitter for directing onto the object at the distal end of said housing an iterative, timed, patterned sequence of light at different wavelengths. An objective lens at said distal end of the housing forms an image in response to the light from said light transmission means, and image transfer apparatus in the housing focuses the image onto a monochrome image intensifier. The image intensifier produces a sequence of intensified monochrome images for each wavelength of light in the pattern that illuminates the object. A video camera connected to the image intensifier and a video processor connected to the video camera integrating the succession of image frames produced during each pattern iteration to produce an integrated color image of the object at the distal end of the endoscope.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
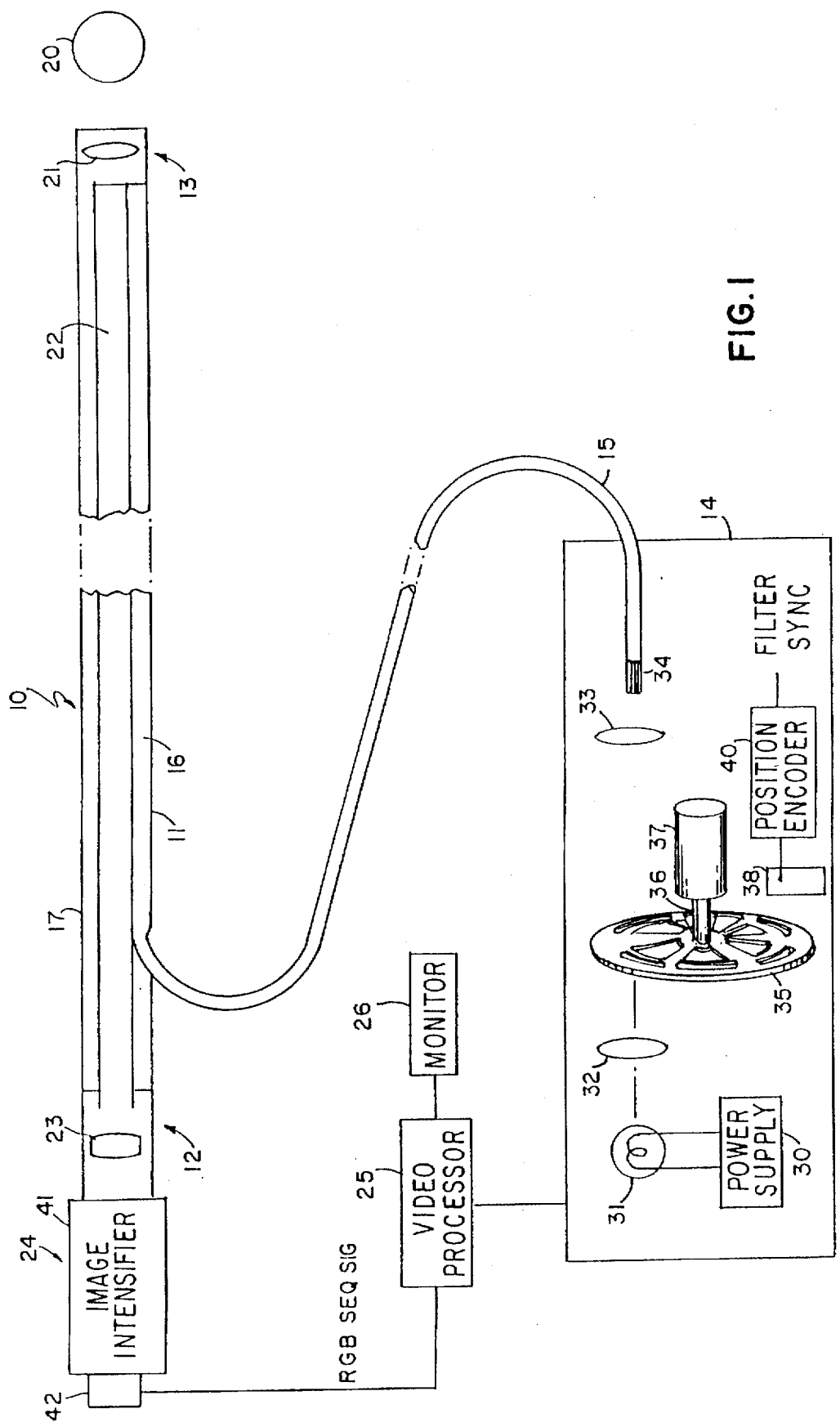
FIG. 1 is a block diagram of a viewing scope apparatus constructed in accordance with this invention.

In FIG. 1 a viewing scope 10, such as a medical endoscope, includes a body portion 11 that extends between a proximal portion at a proximal end 12 and a distal portion at a distal end 13, using "proximal" and "distal" with reference to the individual using the viewing scope 10. The viewing scope is a component of viewing scope apparatus that includes a light source 14 that transmits light at the visible spectrum through an optical waveguide, such as a fiberoptic waveguide 15 that couples to a fiberoptic waveguide 16 within a housing 17. The housing 17 defines the outer surface of the body portion 11.

After the viewing scope 10 is in place, that is, located within a vessel of a patient's body in the case of a medical endoscope, light from the fiberoptic waveguide 16 emerges from the distal end 13 to illuminate an object 20. An objective 21 captures light reflected from the object 20 and forms an image that an image transfer waveguide 22 transfers to an eyepiece 23 at the proximal end 12. The image guide 22 can comprise either fiberoptic cables or conventional lenses. Fiberoptic cables are particularly adapted for use in flexible viewing scopes while conventional lenses are adapted for use in rigid viewing scopes, such as laparoscopes. The eyepiece 23 focuses the image received from the image guide 22 onto a video system 24 that produces an input to a video processor 25. The video processor 25 produces an image on the viewing screen of a video monitor 26.

In accordance with this invention, the light source 14 includes a power supply 30 that energizes a lamp 31. Unlike high-power lamps used in the prior art, the lamp 31 can be a conventional incandescent light bulb that produces a light throughout the visible spectrum. Lenses 32 and 33 focus this light onto an end 34 of the fiberoptic waveguide 15 and direct this light through a color filter wheel 35 that mounts on a shaft 36. A motor 37 drives the shaft 36 and attached filter wheel 35 at a known, substantially constant angular velocity. Indices, described in more detail later, enable a sensor 38 and a position encoder 40 to produce synchronizing signals that provide position and timing information for the video processor 25. This are identified as FILTER SYNC signals in FIGS. 1 and 2.

In general, the filter wheel 35 contains, at discrete angular positions, color filters. Normally the filters are selected from the primary colors. Thus, as the motor 37 rotates the filter wheel 35, the white light from the bulb 30 is converted into an iterative, timed, patterned sequence of light at different wavelengths, normally corresponding to red, green and blue light. The light emerging from the distal end 13 of the fiberoptic waveguide 16 therefore will illuminate the object 20 with the same timed, patterned sequence of light at different wavelengths. Moreover, the same pattern of light at different wavelengths will be coupled as an image to the eyepiece 23.

In accordance with another aspect of this invention, the video system 24 includes an image intensifier 41 and a video camera 42. The image intensifier 41, that preferably is constructed to produce an enhanced output signal for light in the blue wavelengths, increases the brightness of the image obtained from the eyepiece 23. However, due to the monochromatic output of such image intensifiers, the video camera 42 produces a monochromatic image for transfer to the video processor 25. This signal is designated an RGB SEQ SIG signal in FIGS. 1 and 2. It contains color information, but in a time-division multiplexed fashion determined by the rotation and construction of the filter wheel 35.

Figure 2:
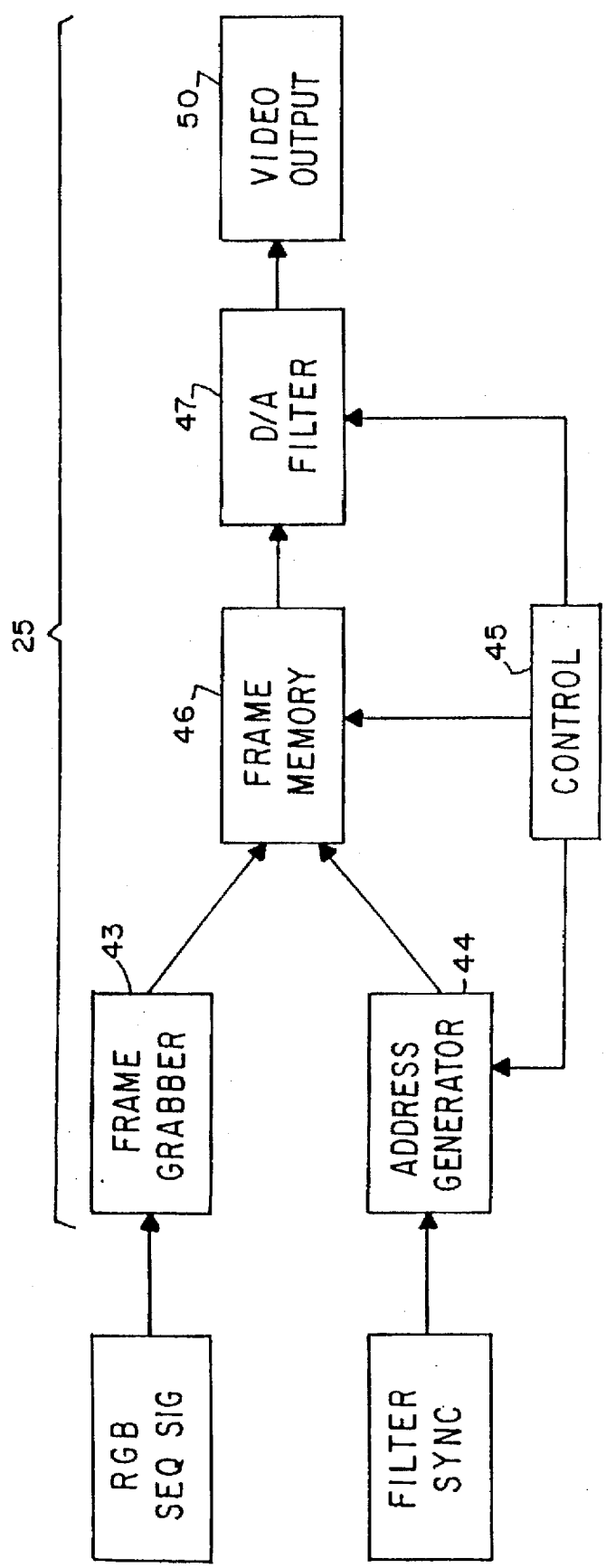
FIG. 2 is a block diagram of a video processor for use in the viewing scope apparatus shown in FIG. 1.

Still referring to FIGS. 1 and 2, the video processor 25 includes a conventional frame grabber circuit 43 that receives the RGB SEQ SIG from the video camera 42 and includes an address generator 44 that receives the FILTER SYNC signals from the light source 14. A control circuit 45 synchronizes the frame grabber circuit 43 with the operation of the filter wheel 35 through the FILTER SYNC signal. More specifically, there are a series of discrete intervals during each revolution of the filter wheel during which the light from the light source 14 is at a constant wavelength corresponding to the particular one of the red, green or blue filters that intercepts the light from the bulb 30 in FIG. 1. Each filter in the filter wheel 35 is sized so that this interval exceeds the time required for the video camera 42 to transmit one frame of image information and for the frame grabber circuit 43 to record all the information for that frame. Each such frame then corresponds to the red, green or blue light component being transmitted by one of the color filters in the filter wheel 35. Thus, the frame grabber circuit 43 produces at its output all the information concerning that color component for one frame. The address generator 44 generates for each color component, an address for a frame memory in a frame memory circuit 46. In one specific embodiment, the filter wheel 35 contains six filter positions in the sequence red-green-blue-red-green-blue. The frame memory circuit 46 contains six sets of memory locations that correspond to each of the six filter positions. As will be apparent, the control 45 and address generator 44 couple the output of the frame grabber circuit 43 to an appropriate set of memory locations in the frame memory circuit 46 in sequence.

The use of the six filter positions and six sets of memory locations enables a digital-to-analog (D/A) filter circuit 47 and video output circuit 50 to produce a color image on the monitor 26 that varies smoothly and naturally. Moreover, with the correct timing, the D/A filter circuit 47 can retrieve the image data from one memory location, such as one red memory location while the information from a succeeding frame corresponding to the red filter can be loaded into the other red memory location.

Thus the viewing apparatus, including the viewing scope 10 shown in FIG. 1 can provide a color image at the monitor 26. The use of the timed, patterned sequence of light of different wavelengths to illuminate an object and the image intensifier and video processor to reconstitute the image allows the apparatus to operate at very low levels of light. For example, it is possible to illuminate vessels in the body with a few watt light bulb as opposed to conventional medical endoscopes in which the light bulbs can be rated as high as 300 or more watts. This reduction in light reduces the cross section of the fiberoptic waveguide 16. Further, the image intensifier increases the effective brightness so that the image transfer waveguide 22 can have a smaller effective aperture. Both these reductions enable the construction of an endoscope with a larger working channel or the construction of a smaller endoscope without reducing the size of the working channel.

Figure 3B:
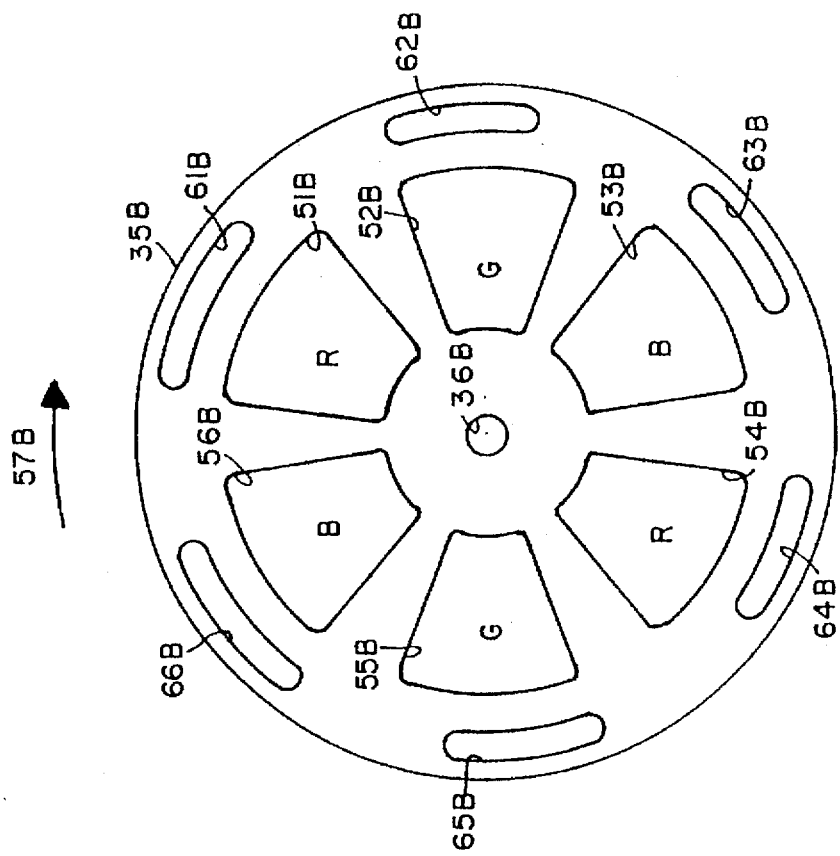
FIGS. 3A and 3B depict alternative embodiments of a color filter wheel that is useful in connection with the viewing scope apparatus of FIG. 1.
Figure 3A:
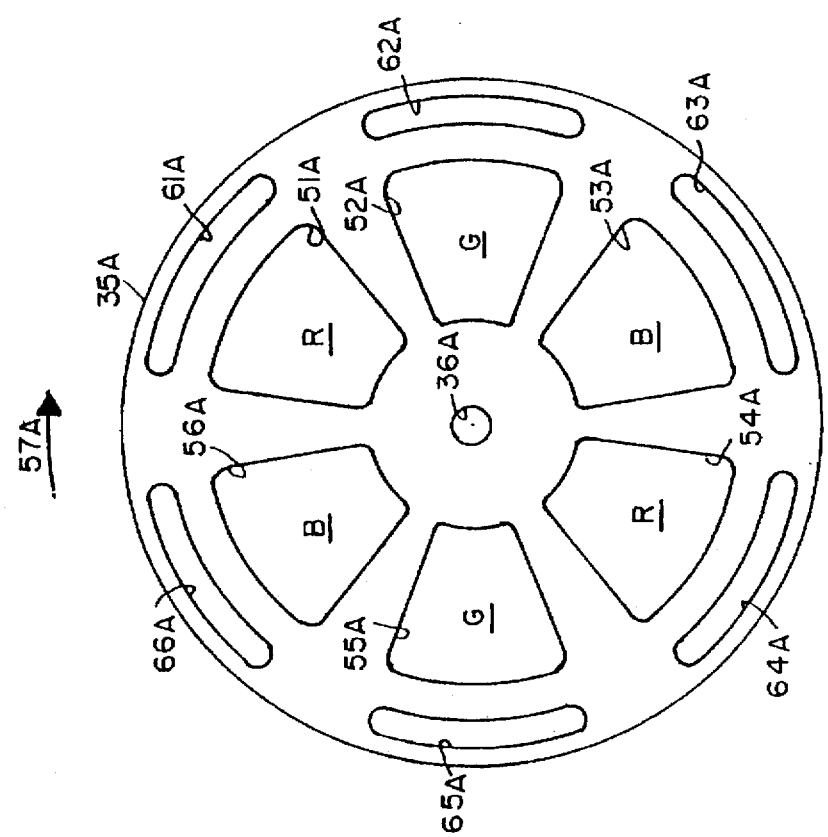

FIGS. 3A and 3B depict filter wheels 35A and 35B that can be substituted for the filter wheel 35 shown in FIG. 1. Each wheel mounts to a central, motor-driven shaft 36A, 36B for rotating the filter wheels 35A, 35B. Each filter wheel is divided into six segments defined as segments 51A through 56A in FIG. 3A and segments 51B through 56B in FIG. 3B. In one specific embodiment, segments 51A, 51B and 54A, 54B are red (R) filters; segments 52A, 52B and 55A, 55B are green (G) filters; and filters 53A, 53B and 56A, 56B are blue (B) filters. If the filter wheels 35A, 35B rotate clockwise in the direction of the arrows 57A, 57B, the wheels convert constant white light from the bulb 30 in FIG. 1 into a sequence of red-green-blue-red-green-blue light pulses. Successive pulses are interrupted when radial portions 60A, 60B between adjacent filters pass the light axis through the lenses 32 and 33 in FIG. 1.

In FIG. 3A, annular slots 61A through 66B constitute indices that enable light from the bulb 30 in FIG. 1 to energize the sensor 38. Thus the sensor 38 will produce a signal indicating the presence of a filter in the light beam. In FIG. 3A each annular slot is angularly coextensive with a filter. Proper location of the sensor 38 then enables the sensor to produce a timing pulse that corresponds to the interval of each monochromatic light pulse from the filter wheel 35A.

FIG. 3B discloses an alternative index construction wherein annular slots 61B through 66B have an angular dimension that is less than the angular extent of the filters. In addition, each annular slot is skewed so that a radius to the center of a filter leads the radius to the center of an annular slot. This provides a time offset to assure that the frame grabber circuit 43 does not initiate its operation until a filter is positioned to provide light of maximum brightness at each of the wavelengths. Typically the interval required for the frame grabber circuit 43 to obtain information for one frame will be less than the time for a filter to pass by the light axis, so the trailing edge of each annular slot, such as slot 61B can extend beyond the corresponding edge of a filter segment.

Figure 4:
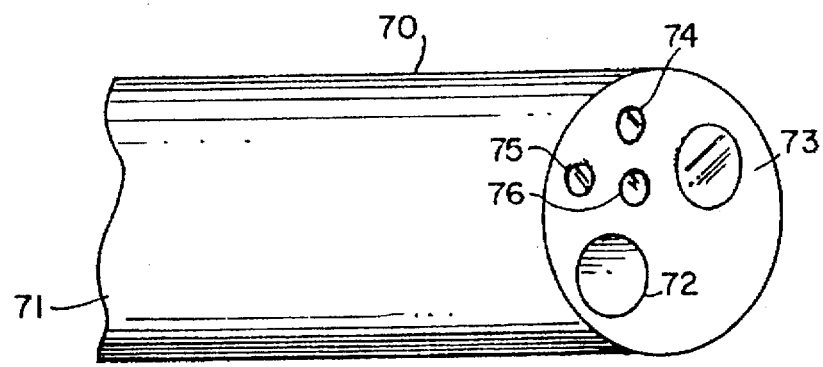
FIG. 4 depicts an alternate illuminating source for the viewing scope apparatus in FIG. 1.

FIG. 4 depicts an alternative light source that could operate in place of the light source 14 and the fiberoptic waveguides 15 and 16. More specifically, FIG. 4 depicts the distal end 70 of a viewing scope 71 with a working channel or lumen 72 and an objective lens 73. In this configuration the light source comprises a light emitting diodes 74, 75 and 76 that are positioned at the distal end directly and connected to a proximal power source through a series of low-voltage conductors (not shown) that connect to a sequencer. The sequencer would energize the light-emitting diodes 74, 75 and 76 in sequence thereby to produce a sequence of monochromatic light pulses for illuminating an object. As will be apparent, such a system eliminates the requirement for a filter wheel and associated mechanisms. Such an illumination system will be particularly valuable when blue light emitting diodes become commercially available. Red and green light emitting diodes now are available. It will also be apparent that this construction will allow an increase in the size of the working channel 72 or allow the viewing scope to add separate working channels. It is also possible that for the same objective lens 73 and related image transfer waveguide the overall size of the endoscope can be reduced.

Figure 5:
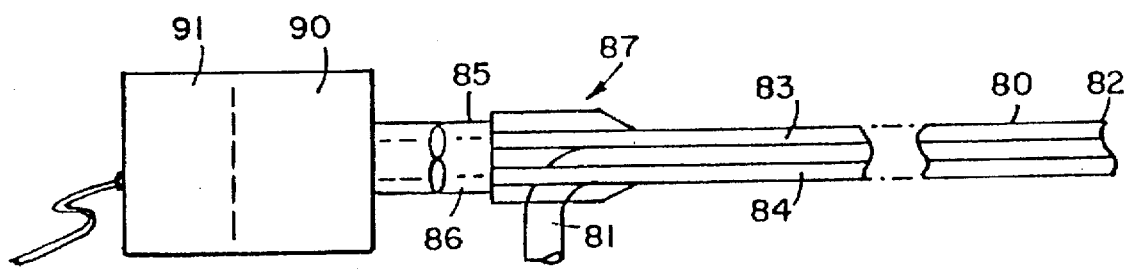
FIG. 5 depicts in schematic form a viewing scope adapted for providing stereo images.

This reduction of the size requirements for the optical assembly also adapts this configuration for stereo imaging. FIG. 5 depicts, in schematic form, an endoscope 80 that includes a fiberoptic waveguide 81 that connects to a light source, such as the light source 14 in FIG. 1. The objective at the distal end 82 produces two images for image transfer waveguides 83 and 84 respectively. Individual eyepieces 85 and 86 at the proximal end 87 of the endoscope 80 focus two distinct images onto an image intensifier 90 that a video camera 91 then transfers to a video processor, such as the video processor 25 in FIG. 1. This system produces two offset images on a monitor. An individual can then, with or without the assistance of stereo glasses, fuse the images into a single image that appears to have three dimensions. As will be apparent, this invention permits such an optical system to be incorporated within a conventionally sized endoscope.

Thus, it is possible to utilize this invention to produce a viewing scope that produces planar or three-dimensional images in color with good brightness, spatial and contrast resolution and color rendition. Images with these desirable characteristics further are obtained using low illumination levels. Low illumination levels limit localized heating at the distal end of any viewing scope and eliminate a need for specialized light sources. Light sources using conventional bulbs with filter wheels or solid-state light sources located at the proximal or distal ends of a viewing scope can provide adequate illumination levels. It will also be apparent that this combination includes individual elements, such as the image intensifier, video camera, video processor and monitor, that are available commercially and that can be combined in a number of different configurations with the attainment of some or all of the advantages of this invention.

Although this invention has been disclosed in terms of certain embodiments, it will also be apparent that many modifications can be made to the specifically disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. Viewing apparatus for viewing from a proximal end thereof an object at a distal end, said viewing apparatus comprising:
   A. light transmission means for directing onto the object an iterative, timed, patterned sequence of light at different wavelengths,
   B. image means for forming at the proximal end an image of the object in response to the light from said light transmission means that reflects from the object,
   C. image intensifier means for producing for each of the different wavelengths in the patterned sequence an intensified monochrome image of the object, and
   D. image processing means connected to said image intensifier means for iteratively processing electronically the succession of monochrome image frames produced during each pattern iteration by said image intensifier means to display an integrated color image of the object at the distal end of said viewing apparatus.

2. Viewing apparatus as recited in claim 1 wherein said light transmission means produces light at wavelengths corresponding to diverse colors and said image intensifier means is characterized by substantially uniform outputs in response to light at each of wavelengths.

3. Viewing apparatus as recited in claim 1 wherein said light transmission means produces light in the wavelengths of red, blue and green light and said image intensifier means provides an enhanced output to blue light thereby to produce a substantially uniform output signal in response to substantially equal brightnesses of light at each of the red, blue and green wavelengths.

4. Viewing apparatus as recited in claim 1 wherein said image processing means comprises means for recording, for each wavelength in the patterned sequence, an image frame from said image intensifier means during the illumination of the object with light of the corresponding wavelength, means for integrating each of the recorded image frames produced during a given iteration of the pattern and means for displaying the integrated images.

5. Endoscopic viewing apparatus for viewing from a proximal end thereof an object at a distal end located in an individual's body, said endoscopic viewing apparatus comprising:
   A. a tubular housing extending between the proximal and distal ends,
   B. light transmission means for directing onto the object at the distal end of said housing an iterative, timed, patterned sequence of light at different wavelengths,
   C. objective lens means at said distal end of said housing for forming a succession of images in response to the light from said light transmission means that reflects from the object, and
   D. image transfer means in said housing for transferring each image in succession formed by said objective lens means to the proximal end of said housing,
   E. image intensifier means for intensifying the succession of images from said image transfer means thereby to produce a series of monochrome output images,
   F. video means connected to said image intensifier means for producing a video signal in response to the series of monochrome output images from said image intensifier means, and
   G. video processing means connected to said video means for integrating the succession of image frames produced during each pattern iteration to display an integrated color image of the object at the distal end of said viewing apparatus.

6. Endoscopic viewing apparatus as recited in claim 5 wherein said light transmission means includes a light source, changeable filter means for producing iteratively the patterned sequence and fiberoptic waveguide means for conveying the patterned sequence of light from said filter means to the objects at the distal end of said housing, said light source and filter means being disposed at the proximal end of said endoscopic viewing apparatus.

7. Endoscopic viewing apparatus as recited in claim 5 wherein said light transmission means includes a plurality of monochromatic light transmission means for generating light at different monochromatic frequency bands and control means for energizing in an iterative fashion said monochomatic light transmission means individually in the patterned sequence, said monochromatic light transmission means being located at the distal end of said housing.

8. Endoscopic viewing apparatus as recited in claim 7 wherein each of said monochromatic light transmission means comprises a light-emitting diode.

9. Endoscopic viewing apparatus as recited in claim 5 wherein said housing comprises a flexible sheath and said image transfer means includes means for focusing the image onto said intensifier means and fiberoptic waveguide means extending between said objective lens means and said focusing means for transferring the image from the distal to the proximal end.

10. Endoscopic viewing apparatus as recited in claim 5 wherein said housing comprises a rigid sheath and said image transfer means includes means for focusing the image onto said intensifier means and a plurality of lenses extending along the length of said rigid housing between said objective lens means and said focusing means.

11. Endoscopic viewing apparatus as recited in claim 5 wherein said light transmission means produces light at wavelengths corresponding to diverse colors and said image intensifier means is characterized by substantially uniform outputs in response to light at each of those wavelengths.

12. Viewing apparatus as recited in claim 5 wherein said light transmission means produces light in the wavelengths of red, blue and green light and said image intensifier means provides an enhanced output to blue light thereby to produce a substantially uniform output signal in response to substantially equal brightnesses of light at each of the red, blue and green wavelengths.

13. Viewing apparatus as recited in claim 5 wherein said video processing means comprises means for recording, for each wavelength in the patterned sequence, an image frame from said video means during the illumination of the object with light of the corresponding wavelength, means for integrating each of the recorded image frames produced during a given iteration of the pattern and means for displaying the integrated images.

14. Endoscopic viewing apparatus as recited in claim 5 wherein said light transmission means includes a filter wheel divided into a plurality of segments, each segment having a filter corresponding to one of the primary colors, said filter wheel additionally including an index that identifies each segment, drive means for rotating the filter wheel about an axis, a light source for directing light through said filter wheel thereby to produce an iterative, timed, patterned sequence of the filtered light at the wavelengths of the primary colors, and a fiberoptic waveguide for conveying the output from said filter wheel through said housing to illuminate the objects with the light from said filter wheel.

15. Endoscopic viewing apparatus as recited in claim 14 wherein said image intensifier means comprises an image intensifier with an enhanced output for blue light.

16. Endoscopic viewing apparatus as recited in claim 15 additionally comprising sequence control means for synchronizing said apparatus, said control means responding to said index means on said filter wheel for controlling said video processing means.

17. Endoscopic viewing apparatus as recited in claim 16 wherein video processing means includes means for storing images for each of the predetermined primary colors and multiplexing means connected to said control means for transferring images from said video means to the corresponding image storage means.

18. Endoscopic viewing apparatus as recited in claim 14 wherein said filter means includes a plurality of filters for each of the primary colors and said filters are sequenced about the filter wheel whereby the wavelengths of light from successive filter positions differs.

19. Endoscopic viewing apparatus as recited in claim 14 wherein said image transfer means additionally includes means at said proximal end of the housing for focussing the image onto said image intensifier means.

20. Endoscopic viewing apparatus as recited in claim 19 wherein said image transfer means includes a pair of image transfer channel means and a pair of means for focusing onto said image intensifier means and wherein said video processing means displays the images as part of a single display.

21. Viewing apparatus for viewing from a proximal end thereof an object at a distal end, said viewing apparatus comprising:

A. light transmission means for directing onto the object an iterative, timed, patterned sequence of light at different wavelengths, B. image means for forming at the proximal end an image of the object in response to the light from said light transmission means that reflects from the object, C. image intensifier means for producing for each of the different wavelengths in the patterned sequence an intensified monochrome image of the object, D. means for converting the sequence of monochrome images from said image intensifier means to a sequence of electrical image frame signals, and E. image processing means connected to said converting means for iteratively processing the succession of image frame signals produced during each pattern iteration by said monochrome image intensifier means to display an integrated color image of the object at the distal end of said viewing apparatus.

* * * * *